United States Patent
Cole et al.

[11] Patent Number: 6,036,458
[45] Date of Patent: Mar. 14, 2000

[54] AUTOMATED PHACO PACK BAR CODE READER IDENTIFICATION

[75] Inventors: Mark S. Cole, Trabuco Canyon; Kenneth E. Kadziauskas, Laguna Niguel; Tom B. Sutton, Huntington Beach, all of Calif.

[73] Assignee: Allergan Sales, Inc., Irvine, Calif.

[21] Appl. No.: 08/943,471

[22] Filed: Oct. 3, 1997

[51] Int. Cl.[7] .................................... F04B 43/12
[52] U.S. Cl. ........................ 417/477.2; 604/111
[58] Field of Search ................ 417/477.2, 279; 604/111, 189

[56] References Cited

U.S. PATENT DOCUMENTS

| | | | |
|---|---|---|---|
| 4,897,789 | 1/1990 | King et al. | 604/6 |
| 5,153,827 | 10/1992 | Coutre et al. | 604/111 |
| 5,324,180 | 6/1994 | Zanger | 417/475 |
| 5,354,287 | 10/1994 | Wacks | 604/232 |
| 5,400,267 | 3/1995 | Denen et al. | 364/552 |
| 5,649,905 | 7/1997 | Zanger et al. | 604/34 |
| 5,697,899 | 12/1997 | Hillman et al. | 604/28 |

FOREIGN PATENT DOCUMENTS

| | | |
|---|---|---|
| 776670 | 4/1997 | European Pat. Off. . |
| 0776670 | 6/1997 | European Pat. Off. . |
| 2110564 | 6/1983 | United Kingdom . |

*Primary Examiner*—Charles G. Freay
*Assistant Examiner*—Robert Z. Evora
*Attorney, Agent, or Firm*—Walter A. Hackler

[57] ABSTRACT

An automated phaco pack identification system in accordance with the present invention generally includes a cartridge or cassette assembly for handling irrigation and aspiration fluids to and from a surgical handpiece, a control console having a drawer or other means for receiving and engaging the cartridge assembly, a computer, and control apparatus, in communication with the computer, for regulating irrigation and aspiration fluid flow. Importantly, the present invention also includes, for example, a bar code element disposed on the cartridge and a bar code reader disposed in the control console for providing an active interface between the cartridge and the computer. The communication feature functions to automatically provide cartridge characteristics, such as serial number and history of the cartridge, through the computer and to a visual display monitor for retrieval by a user of the present invention.

2 Claims, 2 Drawing Sheets

AUTOMATED PHACO PACK BAR CODE READER IDENTIFICATION

The present invention is generally directed to ophthalmic surgical instruments and is particularly directed to disposable or reusable aspiration/irrigation fluid handling cassettes.

In modem surgical practice, many procedures which formerly required large incisions have been replaced by techniques employing microsurgical tools which can be inserted through a relatively small incision and perform a variety of surgical functions therein. For example, prior to the development of microsurgical tools, cataract removal surgery on an eye involved excising a diseased lens by means of a 180° incision about the lens which was thereafter removed intact in order to prepare the eye for the insertion of an artificial replacement lens.

In contrast, phacoemulsification, which involves utilization of a handheld microsurgical tool, is currently one of the most commonly used techniques for removing a diseased lens. The microsurgical tool, commonly known as a phacoemulsification handpiece, generally includes a small diameter tip which may be designed for emulsifying, fragmenting and/or cutting tissue after it is inserted in an incision in the cornea or sclera of the eye. In addition, the tip may include a central channel connected to a source of suction which aspirates the tissue debris from the eye. The handpiece may include lumen for supplying an irrigation fluid, such as a saline solution, to the eye for flushing the eye during the procedure. The excised tissue which is aspirated from the eye along with irrigation fluid is collected in a collection vessel of some type, usually located remote from the handpiece. Thus, the phacoemulsification handpiece typically will perform multiple tasks through a single, small incision.

A control console, remote from the handpiece, is provided which typically includes a source of suction for the aspirating function of the surgical tool, connections to a source of irrigation fluid for the irrigation function of the handpiece, as well as power for driving the cutting or emulsifying aspect of the needle tip. The control console may also be provided with switches for selecting the particular mode of operation of the microsurgical system and with control means to adjust for example, suction level, cutting rate of the tip, and fluid pressure.

At one time, it was standard practice that disposable tubing and hoses extending from the handpiece were individually, manually connected to various pinch valves on the control console prior to the surgical operation. However, this procedure was subject to human error in the placement of the proper tubing to the proper pinch valve and it was also possible for the tubing to become dislodged accidentally. Obviously, the outcome of such error can be devastating during surgery.

More recently, cassettes and cartridges have been developed to simplify the connections required between the handpiece and the console and to reduce the possibility of error. Fluid handling cassettes incorporate part of the connection manifold and may include a collection vessel for aspirated debris and fluid. These cassettes are installed in a reciprocating portion of a control console and when properly secured to the console, the aspiration connections and irrigation connections are automatically engaged. The control console typically includes either a peristaltic pump or diaphragm vacuum pump for providing suction to the aspiration line once the cassette has been installed.

The fluid handling cassettes may be either disposable or autoclavable. An autoclavable cartridge is described in U.S. Pat. No. 5,533,976 to Zaleski et. al., which is hereby incorporated herein by this specific reference thereto. The reusable cartridge is typically flushed clean after use and is then sterilized by autoclaving.

As with any piece of surgical equipment it is of great importance that only thoroughly operable cassettes be used for surgery. Thus it may be preferable to dispose of a cassette after a certain number of uses or after a certain time period of use. Thus, it would be advantageous to have a system in place, of positively and automatically identifying the number of times, or a time period, a particular cassette has been utilized, without the need for manually recording such information.

The present invention improves on conventional phacoemulsification pack systems by providing an active interface between the cartridge and the console such that information about the cartridge may be exchanged with the console, and thereafter become available to the user. The present invention provides an automated system of identifying characteristics of a cassette, including number of uses, length of time of each prior use, and pertinent history about the cassette. Thus, important information regarding the cassette is automatically available to a surgeon. In addition, certain control parameters may be allowed or disallowed depending upon the characteristics of the cassette.

SUMMARY OF THE INVENTION

Accordingly, an automated phaco cartridge system is provided which generally comprises a cartridge assembly for handling of irrigation and aspiration fluids to and from a surgical handpiece. The cartridge assembly may include an irrigation line, an aspiration line and a housing for supporting the irrigation and aspiration lines. The housing includes means, defining openings in said housing means, for enabling access to the irrigation line and aspiration line in order to control fluid flow therethrough.

In addition, the system in accordance with the present invention includes a control console including means for receiving said cartridge assembly. The control console further includes, or is connected to, a computer. Means, responsive to said computer is provided for accessing the irrigation and aspiration lines through the housing openings, in order to coordinate fluid flow through the irrigation and aspiration lines.

Importantly, the present invention further comprises communication means, which will be described in greater detail hereinafter, but generally includes an element disposed on said cartridge assembly and an element disposed in said control console, for providing characteristics of said cartridge assembly to said control console computer.

Preferably, the communication means element disposed on said cartridge assembly comprises a bar code and correspondingly, the communication means element disposed in said control console comprises a bar code reader. When the cartridge has been inserted into the control console, information relating to characteristics of the cartridge is displayed on the monitor. Such characteristics may relate to whether the cassette is a disposable version or an autoclavable version. In addition, while the cartridge is in use, information may be continually recorded and stored in the computer. Thus, when the same cassette is reinserted into the control console, the computer will recognize the serial number of the cassette and retrieve the stored information which may be displayed to the user. Such stored information may relate to a history of the cartridge such as the number of times the cartridge has been used and any problems that had been detected during prior use thereof.

BRIEF DESCRIPTION OF THE DRAWINGS

The present invention will be more clearly understood with reference to the following detailed description when considered in conjunction with the appended drawings of which.

DETAILED DESCRIPTION

Figure 1:
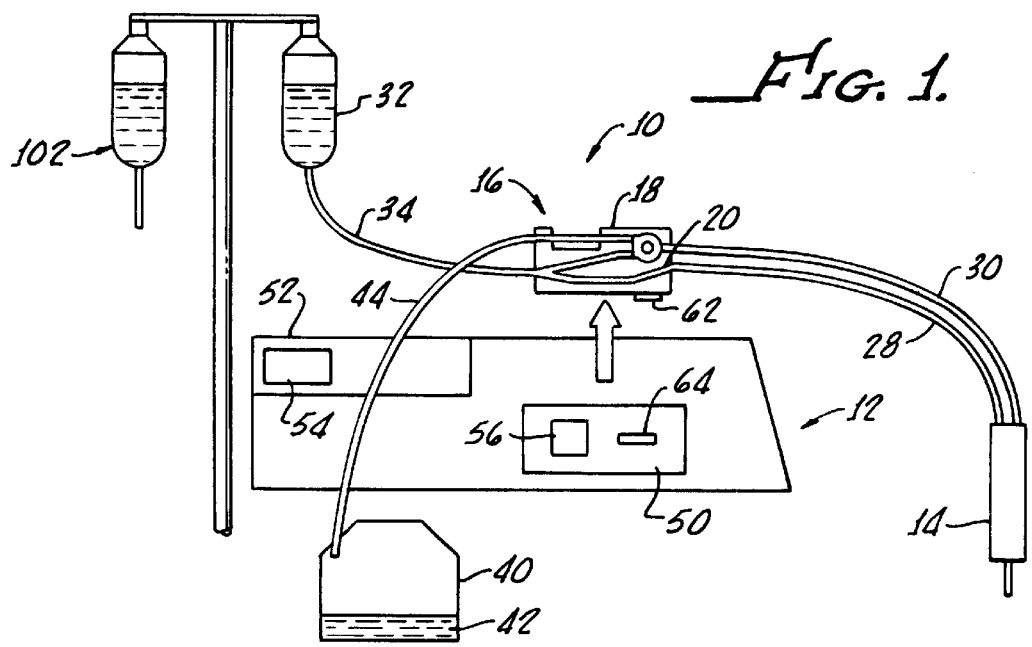
FIG. 1 shows an embodiment of the automatic phaco pack identification system including a cassette which provides an interface between a phacoemulsification handpiece and a control console, the system includes communication means between the cassette and the control console.

Turning now to FIG. 1, an automated phaco pack identification system 10 in accordance with the present invention is shown. The system 10 generally comprises a control cabinet or console 12, a surgical instrument 14, for example a phacoemulsification handpiece, and a cassette or cartridge assembly 16 for handling of irrigation and aspiration fluids to and from the surgical handpiece 14. The cartridge assembly 16 may be disposable or reusable and may be similar to the reusable cartridge assembly described in U.S. Pat. No. 5,533,976 which is hereby incorporated herein by this specific reference thereto.

The cartridge 16 includes a housing 18 having means, such as openings 20 providing access to an irrigation line 28 and an aspiration line 30 which are connected to the handpiece 14. The irrigation line 28 is connected to a source 32 of balanced saline solution (BSS) through a BSS line 34. Fluid pressure within the irrigation line may be controlled by elevation of the source 32.

The cartridge 16 may include a waste receptacle (not shown) within the housing 18, or alternatively a remote waste receptacle 40 for receiving aspirated fluid and tissue debris 42, may be provided through a waste line 44.

The control cabinet 12 includes means, such a drawer 50 for receiving the cartridge assembly 16. It should be appreciated that the cartridge assembly 16, or cassette, may be otherwise engaged to the control cabinet 12 and other suitable configurations as known in the art are possible. In addition, the control console 12 includes a computer 52 and means, responsive to said computer 52, for regulating fluid flow through the irrigation and aspiration lines 28, 30. The computer 52 preferably includes a visual display monitor 54 or other suitable means for displaying information regarding the cartridge 16 to the user.

The means for regulating fluid flow includes a source of suction 56 within the control cabinet 12. When the cartridge 16 is inserted into the console drawer 50, the aspiration line 30 becomes connected to the source of suction 56, which may comprise a peristaltic pump or a diaphragm pump.

Importantly, the present invention further comprises communication means, including an element 62 disposed on said cartridge assembly 16 and an element 64 disposed in said control console 12, for providing characteristics of said cartridge assembly 16 to said control console computer 52.

Figure 2:
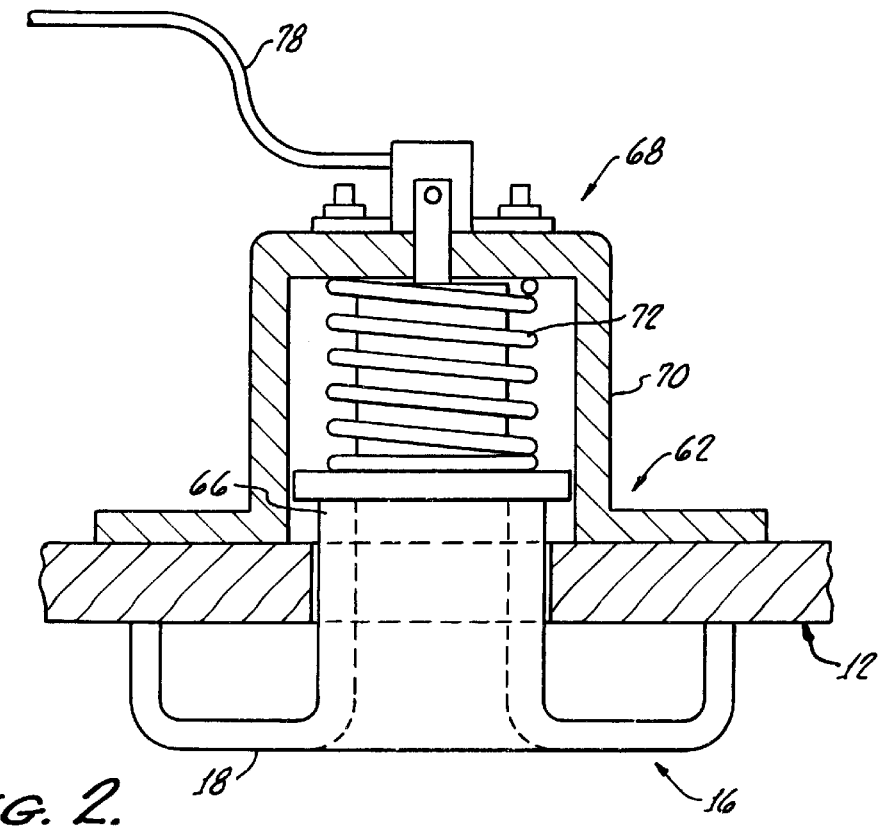
FIG. 2 shows an example of the communication means after the cassette has been installed on the control console, the communication means including a mechanical switch in the cassette and a switch actuator on the control console.

A simple, mechanical version of the communication means feature of the present invention is shown in FIG. 2.

The communication means element 62 disposed on the cartridge assembly 16 may comprise at least one switch 66 and the communication means element 62 disposed in the control console 12 may comprise at least one switch actuator 68. The switch actuator 68 may include a switch housing 70 for a spring 72 or the like which is compressed upon insertion of the cartridge 16 into the control console 12. Sufficient compression of the spring 72 will indicate engagement of the cartridge 16 with the console 12. Electrical leads 78 send a signal to control electronics indicating that the switch or switches has been activated. A single switch embodiment may be used to indicate whether the cartridge is disposable or reusable. Alternatively, a plurality of switches can be provided to indicate additional characteristics of the cartridge 16.

Figure 3:
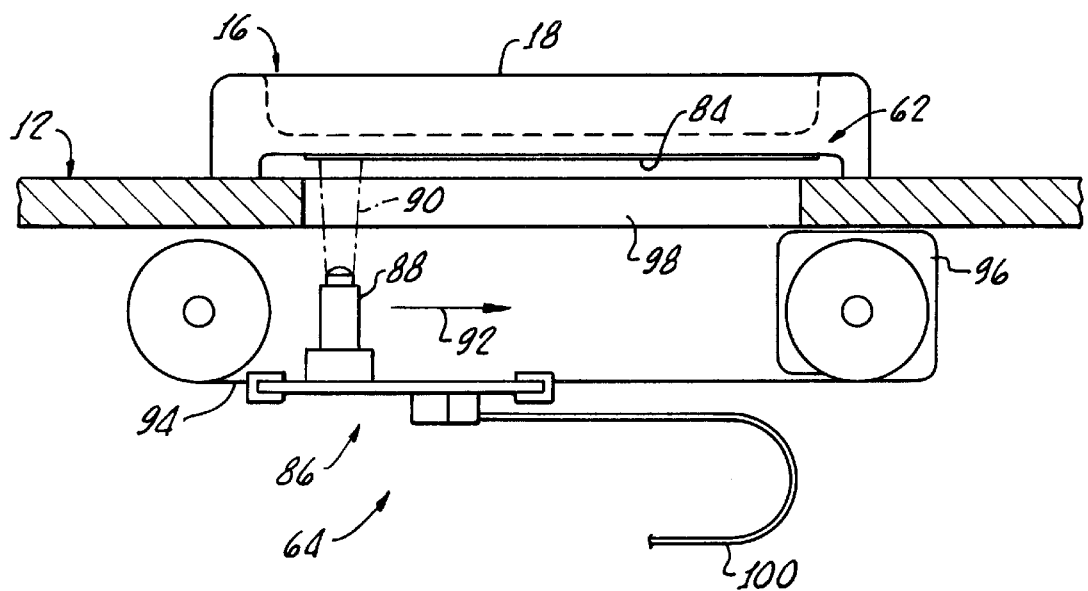
FIG. 3 shows another example of the communication means after a cassette has been installed on the control console, the communication means including a bar code on the cassette and a bar code reader and electronic storage device within the control console

Preferably, alternative to the embodiment shown in FIG. 2, the communication means element 62 disposed on said cartridge assembly 16 comprises a code, for example, a bar code 84, and the communication means element 64 disposed in said control console 12 comprises a bar code reader 86, as shown in FIG. 3. It should be appreciated that other configurations, within the scope of the present invention, are also possible, for example the cartridge element may comprise a magnetic strip and the console element may comprise a magnetic strip reader. For the sake of simplicity however, the remaining description will relate to the embodiment shown in FIG. 3.

The bar code 84 is preferably placed on the cartridge 16 by the cartridge manufacturer. The bar code 84 may comprise, for example, a durable plastic film with indelible code printed thereon. The film is preferably adhered to the cartridge by means of a permanent adhesive.

The bar code reader 86 may include for example a laser scanner 88. Upon insertion of the cartridge 16 into the console 12 the laser scanner 88 is activated by a switch (not shown) which causes a laser 90 to travel in the direction of arrow 92, by means of a coil spring 94 driven by a stepper motor 96 for example, in order to scan and "read" the bar code 84 through a window 98 in the console 12. The information "read" by the scanner 88 is transmitted by suitable means, for example leads 100, to the console electronics and stored in the computer 52 (see FIG. 1). As described above, the information regarding the cartridge 16 will then become available to the user by means of the visual display monitor 54.

The present invention has numerous advantages, some of which will now be discussed. Foremost, the communication means may be utilized for retrieving information from the bar code 84. Such information may include, for example, the system lot number, part number and/or serial number of the particular cartridge or cassette. Another retrievable characteristic may be whether the cartridge is a disposable cartridge, to be used only once, or autoclavable and thus reusable. Thus, upon engagement of the cartridge 16 with the console 12, the computer monitor 54 may automatically display such information.

The present invention provides a unique safety feature that is easy to use and highly reliable. Conventional phaco cartridges and cassettes include identification means consisting of written or typed labels and packaging applied by the manufacturer, which require visual reading thereof by the user. The labels and packaging may become blurred, illegible, torn or otherwise unreliable. This is a problem which occurs most frequently with reusable cassettes or cartridges which are naturally subject to cleaning, resterilization and additional handling, in contrast to cassettes which are used only one time. The present invention overcomes such deficiencies in conventional phaco pack systems by providing a more reliable identification tool which may be used as a primary means of identification.

Other significant advantages of the present invention involve the ability of the phaco pack identification system to automatically and reliably track the history of a particular cartridge. If the cartridge is reusable, each time the cartridge is used, the bar code would be read into the computer and stored therein for later retrieval. The computer may thus be used to track the number of times the particular cassette has been used. In addition, using the same principles, a time period of each use may be tracked and stored.

As a safety feature, information regarding performance of a cartridge during a procedure can be stored into computer memory and retrieved when the cartridge is reinstalled. Thus, in the event the cartridge malfunctions, a warning signal may be displayed on the monitor the next time a user attempts to use the same cartridge.

In addition, the communication means may function to cause automatic purging and cleaning of the cartridge assembly and tubing at the end of a procedure and prior to sterilization if the cartridge is a reusable cartridge. A source of distilled water 102 suspended from a second IV pole mount may be provided to automate this cleaning function; see FIG. 1.

Importantly, the communication means of the present invention can protect against tampering of the cartridge. For example, if the computer is unable to recognize information detected on the bar code, due to unauthorized altering of the bar code, the computer may be caused to automatically reject the cassette.

Advantageously, the communication means element on the cartridge, when read into the computer by the communication means on the cabinet, may be used to automatically set parameters within the control console, such as vibration frequency of the phacoemulsification handpiece needle and suction level. These parameters may represent default parameters suitable for the particular cartridge which may be changed manually by the surgeon. In response to the information on the cartridge, the system could facilitate machine configuration for the user, for example, performance capabilities, and anterior versus posterior surgery.

Similarly, the communication means may function to prevent or disallow various performance perimeters of the system to function depending upon the cartridge configuration. Thus, the present invention also enables a manufacturer of the cartridge to positively prevent use of the cartridge in an unauthorized manner.

In this respect, if a new high performance cartridge is developed, appropriate system parameters and functions may be set by attaching a suitable bar code to the cartridge, eliminating the need for a user to manually set corresponding parameters and functions. This will reduce or eliminate the chance that a cartridge will be used improperly by a user unfamiliar with same. For research and development purposes, performance of a newly developed cartridge assembly can be tracked with the automatic identification system of the present invention.

Although there has been hereinabove described a phaco pack identification system, in accordance with the present invention, for purposes of illustrating the manner in which the invention may be used to advantage, it will be appreciated that the invention is not limited thereto. Accordingly, any and all modifications, variations, or equivalent arrangements which may occur to those skilled in the art should be considered to be within the scope of the present invention as defined in the appended claims.

What is claimed is:

1. In an automated phaco cartridge system having a cartridge assembly for handling of irrigation and aspiration fluids to and from a surgical handpiece, the cartridge assembly having an irrigation line, an aspiration line and a housing for supporting the irrigation and aspiration lines, the housing having openings for establishing fluid flow through the cartridge assembly, and a control console for receiving the cartridge assembly, a computer for regulating the fluid flow through the irrigation and aspiration lines, the improvement comprising an element on the cartridge assembly and an element disposed in the control console, the element providing means for recording each use of the cartridge assembly, tracking a history of each use and providing the history of the cartridge assembly to the control console computer.

2. The system according to claim 1 wherein the element in the cartridge assembly comprises a magnetic strip.

\* \* \* \* \*